(12) United States Patent
Hancock

(10) Patent No.: US 9,381,066 B2
(45) Date of Patent: Jul. 5, 2016

(54) ELECTROSURGICAL INSTRUMENT

(75) Inventor: Christopher Paul Hancock, Bath (GB)

(73) Assignee: Creo Medical Limited, Bath and North East Somerset (GB)

( * ) Notice: Subject to any disclaimer, the term of this patent is extended or adjusted under 35 U.S.C. 154(b) by 289 days.

(21) Appl. No.: 13/976,896

(22) PCT Filed: Jan. 9, 2012

(86) PCT No.: PCT/GB2012/050035
§ 371 (c)(1),
(2), (4) Date: Jun. 27, 2013

(87) PCT Pub. No.: WO2012/095654
PCT Pub. Date: Jul. 19, 2012

(65) Prior Publication Data
US 2013/0274733 A1    Oct. 17, 2013

(30) Foreign Application Priority Data

Jan. 11, 2011 (GB) .................................. 1100443.9

(51) Int. Cl.
*A61B 18/18* (2006.01)
*A61B 18/14* (2006.01)
*A61B 18/00* (2006.01)

(52) U.S. Cl.
CPC ............. *A61B 18/18* (2013.01); *A61B 18/1445* (2013.01); *A61B 18/1815* (2013.01);
(Continued)

(58) Field of Classification Search
CPC .... A61B 18/14; A61B 18/1445; A61B 18/18; A61B 18/1815; A61B 2018/00607; A61B 2018/0063; A61B 2018/0091; A61B 2018/00994; A61B 2018/1861
USPC ...................................................... 606/33–52
See application file for complete search history.

(56) References Cited

U.S. PATENT DOCUMENTS 6,224,593 B1   5/2001   Ryan et al.
6,520,960 B2 *  2/2003   Blocher et al. .................. 606/51
(Continued)

FOREIGN PATENT DOCUMENTS

CN   101278860 A   10/2008
EP   2 174 613 A1   4/2010
(Continued)

OTHER PUBLICATIONS

International Search Report for PCT/GB2012/050035, mailing date Apr. 10, 2012.
(Continued)

*Primary Examiner* — Michael Peffley
*Assistant Examiner* — Khadijeh Vahdat
(74) *Attorney, Agent, or Firm* — Arent Fox LLP

(57) ABSTRACT

A vessel sealing instrument having an instrument tip that comprises a pair of opposing clamping members movable to clamp a vessel to be sealed. The clamping members include an energy delivery structure capable of delivering localized radiofrequency (RF) electromagnetic (EM) energy and microwave EM energy separately or simultaneously into the vessel. The RF EM energy and the microwave EM energy are received in the energy delivery structure from a coaxial cable. Each energy delivery structure comprises first and second conductive elements separated by a planar dielectric layer. The first and second conductive elements are arranged at the opposed surface of the respective clamping member to act as active and return electrodes to transfer RF EM energy into biological tissue by conduction, and as an antenna to radiate microwave EM energy into biological tissue from the opposed surface.

17 Claims, 7 Drawing Sheets

(52) U.S. Cl.
CPC . *A61B2018/0063* (2013.01); *A61B 2018/0091* (2013.01); *A61B 2018/00607* (2013.01); *A61B 2018/00994* (2013.01); *A61B 2018/1861* (2013.01)

(56) References Cited

U.S. PATENT DOCUMENTS

| | | | |
|---|---|---|---|
| 2002/0026127 A1 | 2/2002 | Balbierz et al. | |
| 2007/0225699 A1* | 9/2007 | Goble et al. | 606/34 |
| 2009/0248002 A1* | 10/2009 | Takashino et al. | 606/28 |
| 2009/0248021 A1* | 10/2009 | McKenna | 606/51 |
| 2010/0298822 A1 | 11/2010 | Behnke | |
| 2010/0331838 A1 | 12/2010 | Ibrahim et al. | |
| 2013/0144284 A1* | 6/2013 | Behnke, II | A61B 18/1815 606/33 |

FOREIGN PATENT DOCUMENTS

| | | |
|---|---|---|
| JP | H10-033551 A | 2/1998 |
| JP | 2010-269148 A | 12/2010 |
| WO | WO 2011/010086 A1 | 1/2011 |
| WO | WO 2011/093622 A2 | 8/2011 |

OTHER PUBLICATIONS

Notification of the First Office Action of the corresponding Chinese Application No. 2012800051375, dated Mar. 24, 2015, 6 pages.

Japanese Office Action mailed Nov. 17, 2015 for Japanese Patent Application No. 2013-548888, with English Translation.

* cited by examiner

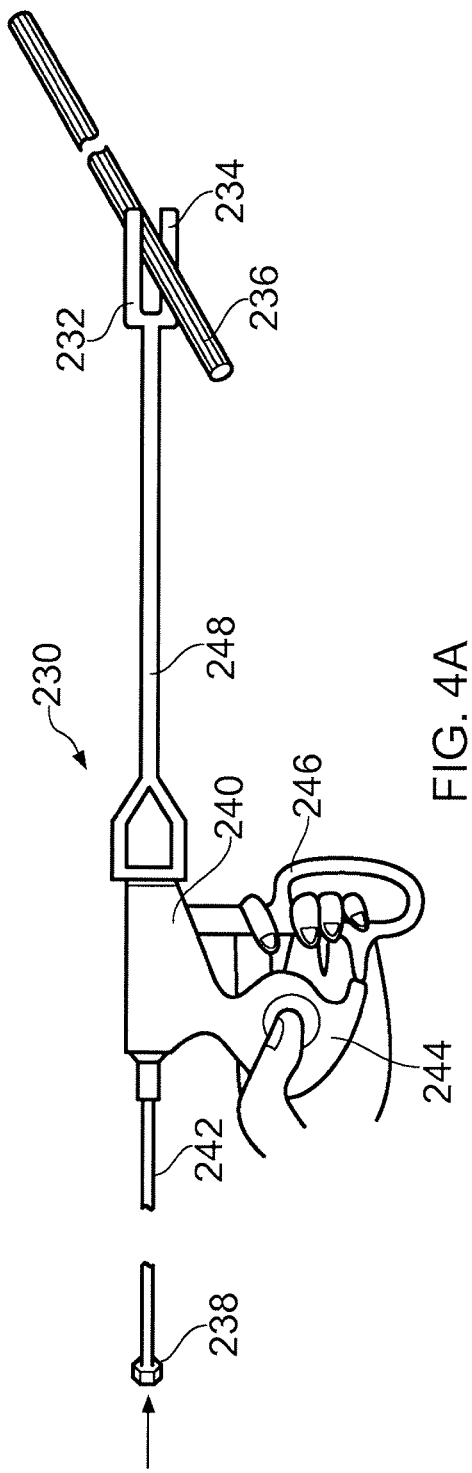
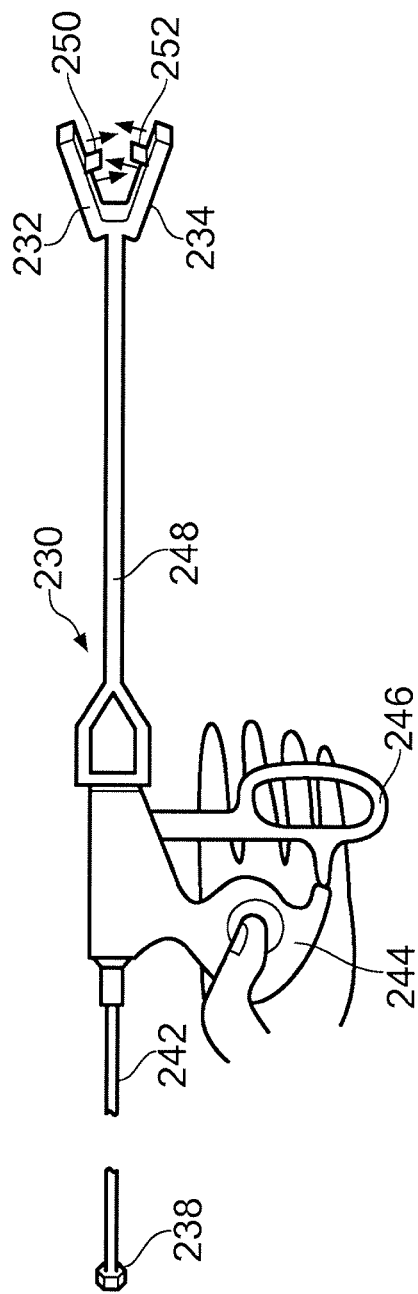
FIG. 4A
FIG. 4B

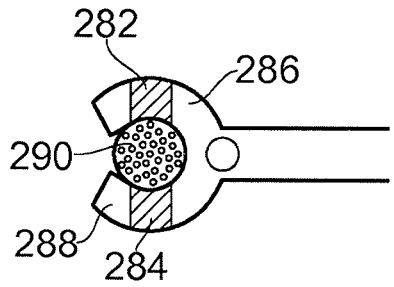
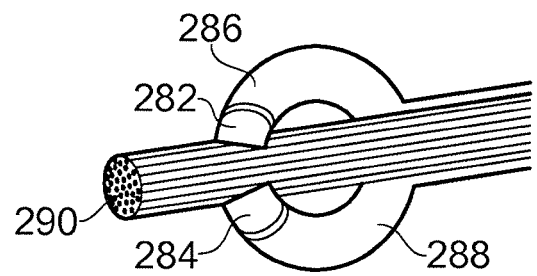
FIG. 7A FIG. 7B
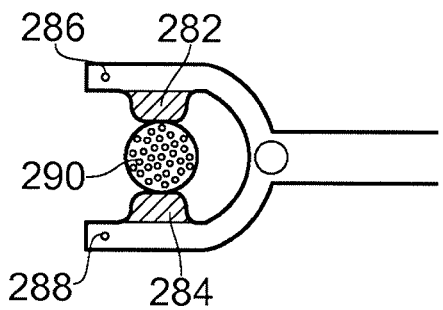
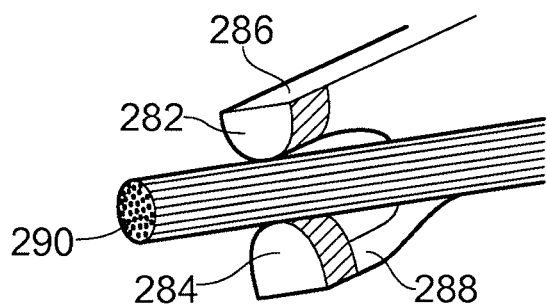
FIG. 8A FIG. 8B
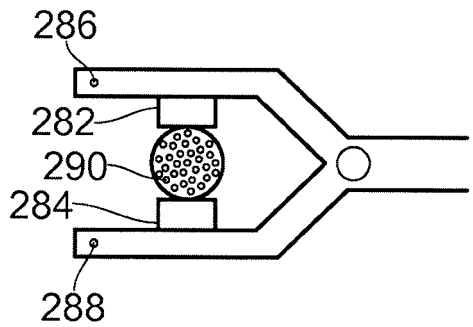
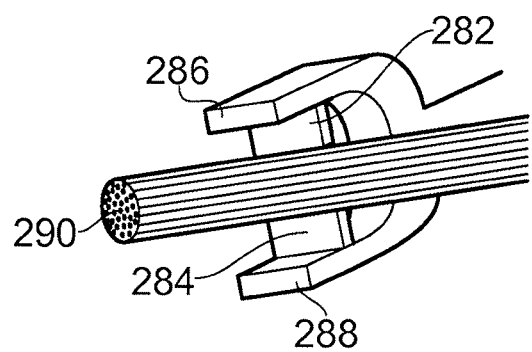
FIG. 9A FIG. 9B

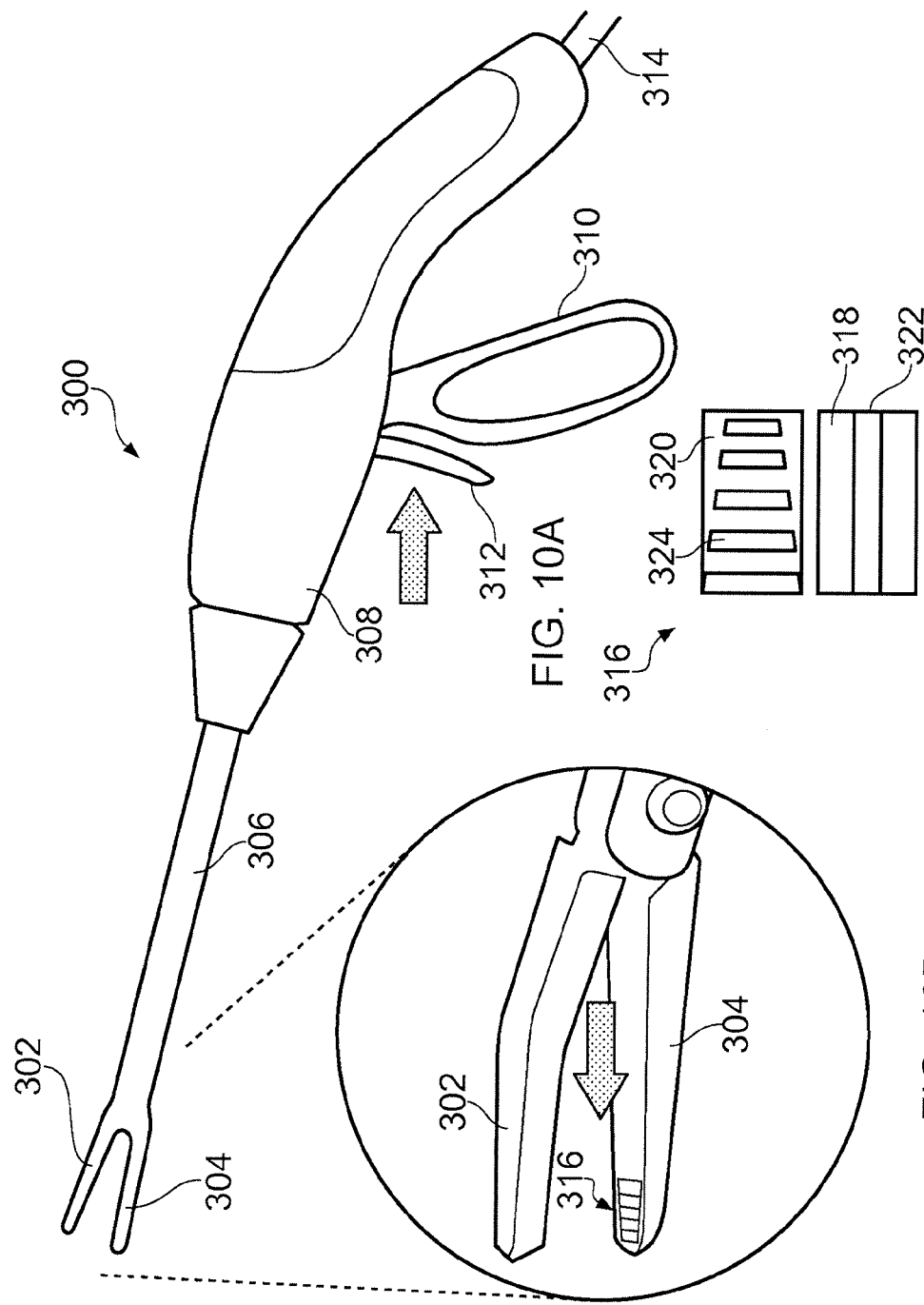

ELECTROSURGICAL INSTRUMENT

CROSS-REFERENCED TO RELATED APPLICATIONS

This application is a National Stage entry of International Application PCT/GB2012/050035 filed Jan. 9, 2012, which claims priority to British Application No. 1100443.9, filed Jan. 11, 2011, the disclosure of each of these prior applications being hereby incorporated in their entirety by reference.

TECHNICAL FIELD

The invention relates to instruments for use with electrosurgical apparatus in which radiofrequency and microwave frequency energy is used to treat tissue. In particular, the invention relates to electrosurgical instruments that are capable of emitting radiofrequency energy for cutting tissue and microwave frequency energy for haemostasis (i.e. sealing broken blood vessels by promoting blood coagulation).

BACKGROUND TO THE INVENTION

Surgical resection is a means of removing sections of highly vascular organs within the human or animal body, such as the liver or the spleen. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting.

For example, the Hemostatix® Thermal Scalpel System (http://www.hemostatix.com) combines a sharp blade with a haemostatic system. The blade is coated with a plastic material and connected to a heating unit which controls the temperature of the blade. The intention is for the heated blade to cauterise the tissue as it is cut.

Other known devices that cut and stop bleeding at the same time do not use a blade. Some devices use radiofrequency (RF) energy to cut and/or coagulate tissue. Other devices (known as harmonic scalpels) uses a rapidly vibrating tip to cut tissue.

Vessel sealing and resection techniques involve the permanent occlusion of vessels, arteries or veins, with a diameter between 1 and 7 mm or greater. The pressure that the seal has to withstand is that of the pumping pressure of the heart.

Vessel sealing is normally a multi-stage process. In a first stage, external pressure may be applied to the vessel wall, to reduce mechanically the volume of tissue, and displace the tissues within the cell wall, so that internal and external vessel surfaces are brought close together. In a second stage, heat may be applied to denature collagen in the vessel walls to cause intermingling of the matrix structure of the inner and outer walls. A third stage of heating may be needed to fix this structure.

If a vessel is to be resected, three seals are normally provided, especially for larger vessels. Two of the seals may be located on the side of the resection location closest to the heart. The vessel is then resected (i.e. divided) with RF energy or a mechanical blade. Subsequent collagenesis causes new fibres to invade the denatured collagen, and the vessel 'grows' in the occluded position.

The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell, which pressure rise cannot be controlled by the cell membrane, resulting in the cell rupturing. When this occurs over a wide area it can be seen that tissue has been transected.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured from a rod like molecule to a coil, which causes the vessel to contract and reduce in size, giving the clot an anchor point, and a smaller area to plug.

If you cut across a vessel, e.g. a veiniole, it bleeds, which then releases fibrinogen to start the coagulation cascade, i.e. heparin, factor 8, etc., with a network of fibrin catching cells, which then forms a soft plug that is invaded by blast cells which create new tissue.

WO 2008/044000 discloses surgical resection apparatus adapted to simultaneously cut and seal highly vascularised tissue, such as the liver or spleen. The apparatus comprising a source of microwave radiation that is coupled to a surgical instrument having an antenna associated with a blade for cutting biological tissue, wherein the antenna is arranged to controllably deliver microwave energy from the source to a region where the blade cuts through tissue. The microwave energy can coagulate blood to effectively seal off the blood flow at the cutting region. WO 2008/044000 suggests the use of high microwave frequencies (e.g. 10 GHz or higher), which offer a particular advantage over the use of known lower microwave frequency ablation systems and radiofrequency (RF) systems due to the limited depth of penetration of the energy by radiation and the ability to enable small sharp blade structures to radiate energy efficiently into the tissue to seal off blood flow by being able to produce uniform fields along the length of the blade whilst at the same time being capable of cutting through the tissue to remove sections of diseased or cancerous tissue.

U.S. Pat. No. 6,582,427 discloses an electrosurgery system arranged to generate both RF energy (typically having a frequency of 1 MHz) and microwave energy (typically having a frequency of 2.45 GHz) for selective operation in a cutting mode or a coagulation mode.

SUMMARY OF THE INVENTION

The present disclosure describes developments of a concept put forward in the applicant's earlier UK patent application no. 0912576.6, filed on 20 Jul. 2009, which is described briefly below with reference to FIGS. 1 and 2.

At its most general, the present invention provides an electrosurgical instrument having an instrument tip that comprises a clamping mechanism (e.g. similar to forceps or surgical scissors) in which one or both opposing clamping members includes an energy delivery structure capable of emitting both localised radiofrequency (RF) electromagnetic (EM) energy and microwave EM energy into the biological tissue. The clamping members may deliver energy separately or simultaneously. The RF EM energy and microwave EM energy may be delivered separately or simultaneously. The RF EM energy may be delivered both in a localised manner (where the active and return electrode are on the same clamping member) and in a more remote manner (e.g. where the active and return electrode are on opposed clamping members).

The electrosurgical instrument of the invention may be used in a surgical vessel sealing procedure, e.g. create a seal that may perform the same task as a clip or ligature across a vessel having a diameter of up to 7 mm. Such a surgical vessel sealing procedure may involve: (i) a mechanical step comprising applying pressure from the clamping mechanism to press the walls of the vessel together so that intra-luminal contents are pushed out sideways leaving the inner and outer vessel walls intact and in contact with one another; (ii) a first electrical heating step comprising applying microwave EM energy and/or RF EM energy having a first waveform for initiating collagen denaturisation and mobilisation of denatured collagen strands; (iii) a second electrical heating step comprising applying microwave EM energy and/or RF EM energy having a second waveform for fixing or fusing the collagen together. The sealing procedure outlined above may precede a cutting procedure that involves a cutting step comprising applying RF EM energy to the vessel from a radiating edge of the instrument. In this process, new collagen can invade the old collagen matrix, whereby the vessel 'grows' in the closed position to produce a permanent seal.

According to the invention, there may therefore be provided an electrosurgical resection (or dissection) instrument for applying to biological tissue radiofrequency (RF) electromagnetic (EM) energy having a first frequency and microwave EM energy having a second frequency higher than the first frequency, the instrument comprising: a handheld body having an elongate probe member extending therefrom, the probe member having at its distal end a instrument tip comprising a clamping mechanism having a pair of opposing clamping members that are movable relative to each other between an open configuration for receiving a biological vessel (e.g. blood vessel) therebetween and a closed configuration for contacting opposite sides of a received biological vessel, wherein one or both of the opposing clamping members includes an energy delivery structure comprising a body made of a first dielectric material, and a first conductive element and a second conductive element which are separated by the first dielectric material; and a coaxial feed cable connected to the handheld body, the feed cable comprising an inner conductor, an outer conductor coaxial with the inner conductor, and a second dielectric material separating the outer and inner conductors, the coaxial feed cable being for conveying to the handheld body, simultaneously or separately, an RF signal having the first frequency and a microwave signal having the second frequency; wherein the inner conductor is electrically connected to the or each first conductive element and the outer conductor is electrically connected to the or each second conductive element to enable one or both opposed surfaces of the instrument tip to emit independently the RF signal and the microwave signal, and wherein the first and second conductive elements are arranged at the opposed surface of the respective clamping member to act: as active and return electrodes to transfer RF EM energy into biological tissue by conduction, and as an antenna to radiate microwave EM energy into biological tissue from the opposed surface.

The energy delivery structure is arranged to provide a localised return path for the RF EM energy, i.e. wherein the return electrode is on the same side of the vessel as the active electrode. Preferably both of opposed clamping members possess such an energy delivery structure, whereby both opposed surfaces of the clamping mechanism can be independently controllable to deliver RF EM energy and/or microwave EM energy into biological tissue.

In an embodiment where only one of the opposed clamping members has an energy delivery structure, the opposing clamping member may have a return electrode formed thereon to provide a more conventional cross-vessel RF return path in addition to the localised RF return path.

The invention may be used to achieve haemostasis on a bleeding liver bed or spleen by applying the radiating blade structure over the bleeding surface to denature collagen in the ends of bleeding vessels to constrict them and make a natural ligature; this can be further plugged by additional coagulation.

The electrosurgical resection instrument may be embodied as a vessel sealing device, in which the microwave EM energy is used to coagulate biological fluid (e.g. blood) flowing in a vessel (e.g. vein, artery or the like) held within the clamping mechanism in the closed configuration. The clamping mechanism may also be used to apply pressure to the vessel to play a part in the overall sealing process, especially in the instance where the vessel is to be divided into two parts and each end needs to be plugged to prevent blood loss. The coagulated fluid may act as a plug to block fluid flow in the vessel. This plug of denatured tissue may be formed using a microwave field with a depth of penetration suitable to produce a plug that forms a permanent seal by creating the condition that allows new fibres to invade collagen that has been denatured using the focussed microwave field to enable the vessel to 'grow' on the occluded position. The distribution of the EM field inside the tissue is such that the energy and cellular destruction reduces with distance and at the preferred frequency of operation, this field has reduced to 37% of its maximum value over a distance of between 6 mm and 7 mm and the decay is exponential. The RF EM energy may then be applied to cut through the vessel. The sealing and cutting may be performed solely by the RF and microwave EM energy whereby the microwave energy is used to seal and the RF energy is used to cut; the clamping mechanism need not (and preferably does not) have sharp surfaces for slicing through tissue, and the minimum distance between the opposed surfaces in the closed configuration may be set to be above a threshold value to prevent unwanted physical pressure being applied to the vessel. A force may be applied to the vessel to assist with the sealing process.

The first and second conductive elements and the first dielectric material on each clamping member may form a bipolar emitting structure, each with their own local preferential return path. This means that each clamping member may act as a radiator that can independently radiate RF and microwave energy into tissue and does not rely on a remote return pad/plate or second electrode on a separate clamping surface.

The opposed surfaces of the clamping members (i.e. the vessel contact surfaces) may be rounded or curved at the ends, i.e. contain no sharp edges, whereby biological tissue (i.e. a blood vessel) is clamped between rounded edges to deliver microwave and RF energy into a vessel to enable the vessel to be cut and sealed at the same time. The shape of the opposed surface may be flat, concave or convex. If concave or convex, the radius or curvature may be chosen based on the diameter of the vessel that the instrument is intended to seal. Matching the radius of curvature of the opposed surfaces to the vessel to be treated may ensure that the instrument can deliver microwave energy into the vessel with an adequate thermal margin to ensure that when the RF energy is deployed to cut the vessel (at the centre of the denatured region), there is enough coagulated tissue to ensure that the vessel is adequately sealed and that the seal cannot break, i.e. the plug is sufficient in size and formed in such a manner so as to ensure that the vessel is permanently sealed and the process of growing new tissue is promoted. For example, a 4 mm diameter vessel may use radiators with a 8 mm radii, whereas a 6 mm vessel may use radiators with a 12 mm radii. In this arrangement, the RF energy cuts the tissue at the centre of the coagulated region. The radiation pattern produced by the microwave radiation may be omni-directional, whereby the shape of the denaturisation volume may be spherical. In this situation, the depth of denatured or reformed tissue will be similar to the width of the plug or the denatured tissue penetrating into the side walls of the vessel either side of the vessel being parted, i.e. the depth of penetration downwards will be the same as that penetrating into the ends of the parted vessel. The field propagating into the vessel forms the plug. The formation of the plug produced by the microwave field will be exponential and the depth of penetration of the tissue that is denatured will depend upon the frequency of the microwave energy. The depth of penetration, defined as the distance of propagation into the biological tissue where the field has decayed to 37% of its maximum value is preferably between 6 mm and 7 mm for blood vessels and blood at the preferred frequency of operation. Since it is the focussed heat that is responsible for the shape of form of the denatured tissue that produces the seal, the heating profile should follow the profile of the electromagnetic field propagating inside the tissue to give the preferred shape or distribution of denatured tissue. The depth of penetration at the preferred frequency of operation may help promote the formation of a permanent seal using this invention.

Table 1 provides a list of representative tissue structures involved with the resection and sealing applications addressed by this application and the respective depths of penetration of the microwave field at 5.8 GHz.

TABLE 1

Representative tissue types and depth of penetration at 5.8 GHz

| Tissue type | Depth of penetration of E field (mm) |
| --- | --- |
| Blood vessel | 7.667 |
| Blood | 6.019 |
| Liver | 7.1829 |
| Spleen | 6.5206 |

This information indicates that the desirable extent of both the downward action (i.e. across the vessel) used to assist with the transecting process and the sideways action (i.e. longitudinally along the vessel) used to create the plug is between 6 mm and 7 mm.

The rise in temperature of the tissue during the initial period of energy absorption is linearly proportional to the value of the specific absorption rate (SAR), which itself is proportional to the square of the induced electric field, therefore the temperature rise within the tissue is proportional to the square of the electric field, which decays in an exponential manner in accordance with the depth of penetration inside the tissue. This information can be used to estimate (e.g. in advance) the formation and depth of the plug that will be formed to seal the vessel.

The clamping mechanism may resemble surgical scissors or forceps or other conventional cutting device structures. The opposed surfaces of the clamping member in such cases may be arranged along the edges of the blades of the cutting structure. In one embodiment, the first dielectric material is a planar sheet and the first and second conductive elements are conductive layers formed on opposite sides of the planar sheet. The RF EM energy and microwave EM energy may be emitted at an edge of this layered structure (also referred to as a parallel plate radiating structure) that is exposed at one of the opposed surfaces of the clamping mechanism.

Preferably, the exposed edge of the layered structure is aligned with the length of the clamping member (e.g. aligned with its respective surgical scissor blade). In this arrangement the plane of layered structure is parallel to the plane in which the clamping members move relative to one another between the open and closed configuration. This arrangement offers the advantage of being able to seal vessels of any length, i.e. the position where the vessel is sealed is not limited by the length of the arms of the cutting device. This also offers advantage in terms of minimising the overall size of the sealing device, which is desirable in terms of being able to manipulate the device within the body with ease and enabling the device to be used in regions of the body with limited access or visibility.

However, in other embodiments the exposed edge of the layered structure may be angled with respect to the length of the clamping member, e.g. it may be perpendicular thereto.

Each clamping member may have a plurality of layered structures arranged along its respective opposed surface, in order to increase the area of coverage or the size of the vessel that can be sealed.

In another embodiment, the first dielectric material and the first and second conductive elements may be arranged as a travelling wave antenna. Here the first conductive element may be a layer of metallisation covering an outward facing surface of the first dielectric material at the respective opposed surface of the clamping member. A plurality of slots may be formed in the layer of metallisation to expose the first dielectric material. The second conductive element may be a feed line formed on the opposite surface of the first dielectric material from the layer of metallisation. The length of the slots (i.e. radiating aperture) may increase towards the distal end of the instrument tip (i.e. with increasing distance from the feed point) in order to ensure a uniform field is produced. The slots may be arranged along the length of the clamping member or perpendicular to it.

The handheld body may comprise a clamp operating actuator, e.g. a finger operated lever or the like, for moving the clamping members relative to one another. The clamp operating actuator may be conventional. Preferably, the instrument includes an energy activation switch that is operable independently of the clamping to activate energy delivery from the opposed surfaces of the clamping mechanism. The activation switch may be a finger operated trigger on the handheld body, or may be a separate footswitch.

The coaxial feed cable may extend through the housing to the instrument tip. The elongate probe member may comprise a shaft (e.g. a rigid hollow tube) for housing the feed cable. The clamping mechanism may include a hinge about which the opposed clamping members pivot. The coaxial feed cable may connect to a power splitting arrangement at the hinge, which operates to split the RF EM energy and/or microwave EM energy conveyed by the feed cable between the radiating structures on each clamping member. The power splitter arrangement by include one or more 3 dB power splitters (the number of splitters needed will depend on the number of radiating structures that need feeding). Preferably the power splitting arrangement is configured to deliver an equal power share to each radiating structure. Each power share is preferably in phase to promote a uniform tissue effect at the opposed surfaces. In the instance where only one radiating structure is used in the embodiment, the power splitter will not be required.

The clamping mechanism may comprise more than one pair of opposed clamping members. For example, there may be two pairs of opposed clamping members whose clamping directions are orthogonal. With this arrangement the vessel is surround on four sides, which may facilitate rapid and uniform denaturisation of collagen or the formation of a plug to seal the vessel.

In certain instances, especially where large diameter vessels are to be permanently occluded, it may be necessary to use the instrument to initially apply external pressure to the vessel walls to mechanically reduce the volume of tissue and displace the tissue within the cells wall to bring internal and external surfaces of the vessel in close proximity. Collagenesis then causes new fibres to invade the denatured collagen, and the vessel 'grows' to the occluded position.

Microwave energy and/or RF energy may then be applied to denature collagen in the vessel walls, and to cause intermingling of the matrix structure of the inner and outer walls. A further application of microwave energy may then be applied in order to fix the structure.

For larger vessels, i.e. with an outer diameter of 5 mm or more, three seals are often performed; two being made at the end closest to the heart and one at the other end. In one embodiment, the instrument according to the invention may produce two plugs in a single operation, and the cut may be performed in the region between the plugs. In practice, it may be desirable to perform the RF cut once the two plugs have been formed using the microwave energy ensure the vessel has been successfully plugged prior to cutting through or dividing it into two parts. The seals or plugs may be produced solely using the focussed microwave energy and following the application of the microwave energy, RF energy may be applied to the blade to divide the vessel into two parts. Subsequent collagenesis then causes new fibres to invade the denatured collagen, and the vessel then 'grows' to the occluded position.

Thus, the present invention may provide a vessel sealing and cutting instrument having one or more pairs or opposed clamping members, each of which have a parallel plate radiating structure fed using a balanced power splitter where more than one radiating structure is used. In one embodiment, four parallel plate radiating structures may radiate 10 W each or two parallel plate radiating structures may radiate 20 W each. Fluid within a blood vessel located between the radiating surfaces can be coagulated using microwave energy to permit the vessel to be cut (sealed) without loss of blood. The ability to radiate both RF EM energy (to cut) and microwave EM energy (to coagulate and create a plug by denaturing the collagen structure) from each parallel plate arrangement in an independent manner, i.e. the field distribution is independent of the size of the vessel or the distance between the radiating edges of the two radiators, means that the efficiency of the instrument is not compromised or limited by the size (diameter) of the vessel.

The size of the elongate probe member and clamping mechanism may depend on the application for which the instrument is required. For example, the instrument may be used in open surgery, laparoscopic surgery, NOTES, TEMS, and single port laparoscopic surgery.

Herein, the first frequency may be a stable fixed frequency in the range 10 kHz to 300 MHz and the second frequency may be a stable fixed frequency in the range 300 MHz to 100 GHz. The first frequency should be high enough to prevent the energy from causing nerve stimulation and low enough to prevent the energy from causing tissue blanching or unnecessary thermal margin or damage to the tissue structure. Preferred spot frequencies for the source of energy at the first frequency include any one or more of: 100 kHz, 250 kHz, 500 kHz, 1 MHz, 5 MHz. Preferred spot frequencies for the source of energy at the second frequency include 915 MHz, 2.45 GHz, 5.8 GHz, 14.5 GHz, 24 GHz.

The use of a single frequency source with a small drift around the centre frequency for generation of the microwave energy, i.e. 5.8 GHz+/−100 KHz, may offer advantage in terms of making the instrument more selective as this implies the antenna structures used to deliver the microwave energy into the tissue can be made with a high Q, where Q is defined as the ratio of the centre frequency divided by the 3 dB bandwidth or the ratio of the energy stored to the energy loss per cycle. A high Q structure implies that it will be matched only to a narrow range of impedances. This means that the structures introduced here may be well matched to particular tissue impedance, which implies that the structure will couple energy efficiently into certain tissue types, but not others. This is advantageous in terms of the instrument being selective and will only deliver energy into biological tissue that requires treatment.

BRIEF DESCRIPTION OF THE DRAWINGS

Embodiments of the invention are discussed in detail below with reference to the accompanying drawings, in which:

FIG. 4A is a vessel sealing instrument for coagulating and cutting vessels that is another embodiment of the invention, wherein the clamping radiating blades are closed and in contact with a vessel;

FIG. 4B is the vessel sealing instrument of FIG. 4A wherein the clamping radiating blades are open;

FIGS. 7A and 7B are a side view and perspective view respectively of a vessel sealing instrument that is an embodiment of the invention, wherein the clamping radiating blades have a concave shape;

FIGS. 8A and 8B are a side view and perspective view respectively of a vessel sealing instrument that is an embodiment of the invention, wherein the clamping radiating blades have a convex shape;

FIGS. 9A and 9B are a side view and perspective view respectively of a vessel sealing instrument that is an embodiment of the invention, wherein the clamping radiating blades are flat;

FIG. 10A is a schematic view of a handheld vessel sealing instrument that is another embodiment of the invention;

FIG. 10B is a close up view of the clamping radiating blades of the vessel sealing instrument shown in FIG. 10A;

FIG. 10C is a schematic view of a travelling wave antenna structure fabricated onto the clamping radiating blades shown in FIG. 10B.

DETAILED DESCRIPTION; FURTHER OPTIONS AND PREFERENCES

Figure 1:
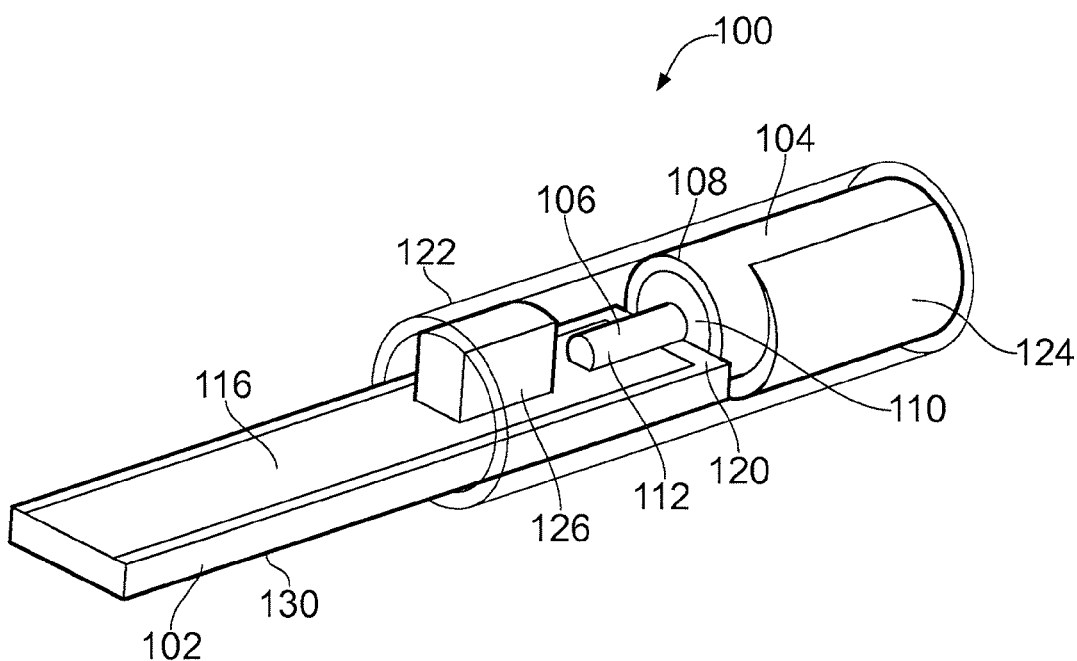
FIG. 1 is a top perspective view of a instrument that may be useful for understanding the invention.

As mentioned above, the disclosure herein relates to developments of a concept put forward in the applicant's earlier UK patent application no. 0912576.6, filed on 20 Jul. 2009, and incorporated herein by reference. UK patent application no. 0912576.6 describes an electrosurgical instrument in the form of a spatula comprising a planar transmission line for carrying microwave energy formed from a sheet of a first dielectric material having first and second conductive layers on opposite surfaces thereof, the planar transmission line being connected to a coaxial cable that is arranged to deliver microwave energy to the planar transmission line, the coaxial cable comprising an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The first conductive layer is spaced from the end of the transmission line that abuts the coaxial cable to electrically isolate the outer conductor from the first conductive layer, and the width of the first and second conductive layers is selected to create an impedance match between the transmission line and the coaxial cable. The spacing between the end of the outer conductor of the transmission line and the first conductive layer also determines the impedance match between the microwave source and the tissue load. The spatula configuration set forth in UK patent application no. 0912576.6 provides desirable insertion loss between the co-axial feed line and the end radiating section, whilst also providing desirable return loss properties for the edges of the spatula when in contact with air and biological tissue respectively. In more detail, the insertion loss along the structure may be less than 0.2 dB at the frequency of interest, and the return loss less than (more negative than) −3 dB, preferably less than −10 dB. These properties may also indicate a well matched junction between the coaxial cable and the transmission line spatula structure, whereby microwave power is launched efficiently into the spatula. Similarly, when the edges of the spatula are exposed to air or biological tissue that is not of interest, the return loss may be substantially zero (i.e. very little power radiated into free space or undesirable tissue), whereas when in contact with desirable biological tissue the return loss may be less than (more negative than) −3 dB, preferably less than −10 dB (i.e. the majority of power in the spatula is transferred to the tissue). The instrument discussed in UK patent application no. 0912576.6 is intended to radiate microwave energy from the edges of the planar transmission line to cause localised tissue ablation or coagulation or denaturisation of the tissue.

However, UK patent application no. 0912576.6 also discloses that the spatula discussed above may have an RF cutting portion integrated therewith. The RF cutting portion may be formed by using the first and second conductive layers mentioned above as active and return electrodes for RF energy. This arrangement may take advantage of the fact that the active and return electrodes are in close proximity to one another, thus setting up a preferential return path to enable local tissue cutting action to take place without the need for a remote return pad or a highly conductive liquid, i.e. saline, existing between the two electrodes.

In this example, the RF cutting portion may comprise a RF voltage source coupled to the planar transmission line, a frequency diplexer (or signal adder) comprising a low pass filter to prevent the high frequency microwave energy from going back into the lower frequency RF energy source and a high pass filter to prevent the lower frequency RF energy from going back into the higher frequency microwave energy source. In one example, the frequency diplexer may be used to enable the microwave and RF energy sources to be combined at the generator and delivered along a single channel, e.g. co-axial cable, waveguide assembly or twisted pair, to the spatula structure. The RF cutting energy may be delivered solely into the tissue or may be mixed or added with the microwave energy and delivered simultaneously to set up a blended mode of operation.

Figure 2:
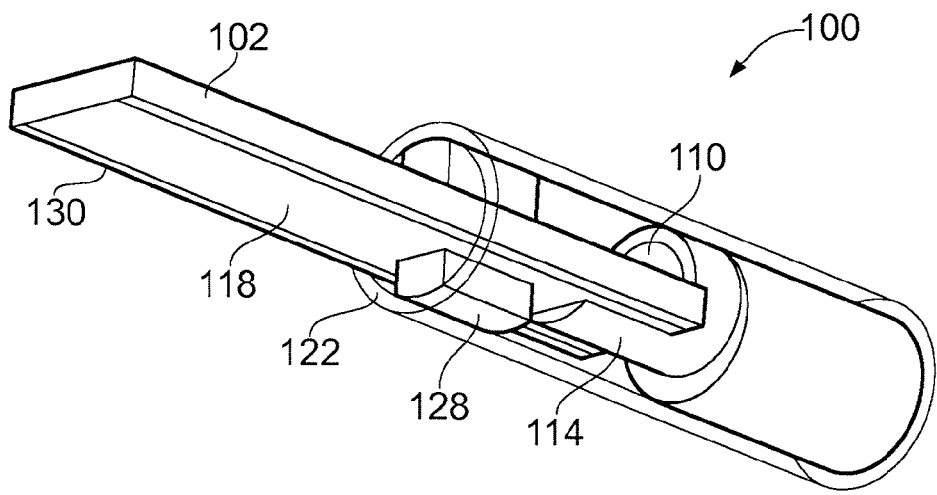
FIG. 2 is a bottom perspective view of the instrument shown in FIG. 1.

A detailed example of the spatula configuration having a bipolar antenna structure as described in UK patent application no. 0912576.6 is shown in FIGS. 1 and 2. FIG. 1 shows a instrument 100 having a 0.6 mm thick transmission line 102 connected to a coaxial cable 104. The instrument is suitable for operation at 2.45 GHz, 5.8 GHz and 14.5 GHz. The coaxial cable 104 comprises an inner conductor 106, an outer conductor 108 and a dielectric material 110 separating the inner and outer conductors 106, 108. At the distal end of the coaxial conductor 104, the inner and outer conductors 106, 108 have protruding portions 112, 114 which extend away from the dielectric material 110. The transmission line 102 is sandwiched between the protruding portions 112, 114 so that its proximal end abuts the distal end of the coaxial cable. The protruding portion 112 of the inner conductor is arranged to contact an upper conductive layer 116 of the transmission line 102 and the protruding portion 114 of the outer conductor is arranged to contact a lower conductive layer 118 of the transmission line 102.

A gap 120 is provided between the proximal edge of the upper conductive layer and the distal end of the coaxial cable to prevent shorting between the inner and outer conductors and to help with the impedance match between structure (that forms a part of the source) and the load impedance presented to the radiating structure by the biological load.

A plastic tube support 122 (shown as translucent for convenience) is mounted over the junction between the transmission line 102 and the coaxial cable 104. The inner diameter of the tube support 122 is greater than the outer diameter of the coaxial cable 104 to enable it to be fitted over the cable. A mounting structure 124, e.g. glue or the like, is attached between the coaxial cable 104 and the tube support 122 to secure the cable in place. Similarly, mounting blocks 126, 128 (e.g. glue) are attached between the transmission line 102 and the tube support 122 to secure the transmission line in place.

The transmission line may comprise a 0.61 mm thick sheet 130 of TRF-41 (dielectric constant 4.1 and loss tangent 0.0035). The coaxial cable 104 has an outer diameter of about 2.2 mm and a pin diameter of 0.574 mm. The coaxial cable 280 used in the model used to develop a structure that can efficiently radiate microwave energy into tissue from one or both sides and/or from the distal end is UT 85C-LL (from Micro-Coax).

The conductive layers 116, 118 on the transmission line 102 go right to the distal end of the sheet 130 and are 2.002 mm wide. The sheet 130 is 2.6 mm wide, although in the invention this may be reduced to 2 mm or less.

The tube support 122 is a polypropylene tube having an outer diameter of 3.1 mm, to be a good sliding fit in an endoscope, and inner diameter of 2.6 mm. This gives a wall thickness of about 0.25 mm. The material and thickness is not critical; nylon or polythene may be used, or a number of other plastics. The edges of the transmission line may be chamfered so that the instrument will sit in place just below the diameter of the tube.

The tube comes 5 mm along the length of the transmission line 102. The overlap with the coaxial cable is 5 mm here but can be as long as required. It is preferable for the tube to be short enough to get through a bent endoscope. The main purpose of the tube is to support the instrument and to hold it steady in the end of the endoscope.

The mounting structure 124 and mounting blocks 126, 128 may be made of almost any material that is biocompatible and can be used to hold the structure in place, since these materials do not affect the performance of the instrument if kept away from the instrument edges and the pin of the coax.

The gap 120 between the upper conductive layer 116 and the coaxial cable is 0.5 mm. This gap is also ensures that the impedance of the radiating structure is matched to the impedance of the tissue load.

The centre of the instrument is offset by about 0.5 mm (0.53 mm) from the centre of the coaxial cable. The axis of the outer tube is about 0.3 mm above the centre of the instrument, but only needs to fit over components in the assembly and hold them steady.

The dielectric sheet 130 may be just over one quarter or three quarters of a wavelength long at the preferred frequency of operation (e.g. 8 mm or 21 mm) so that a standing wave will not couple strongly to a supporting plastic tube near the base of the instrument.

The present invention utilises antenna structures similar to those described above to provide independent radiating edges (referred to herein as "blades", although they need not be sharpened) in a clamp-like instrument structure that can be used to hold the vessel and apply a level of force to the outer wall if required.

Figure 3A:
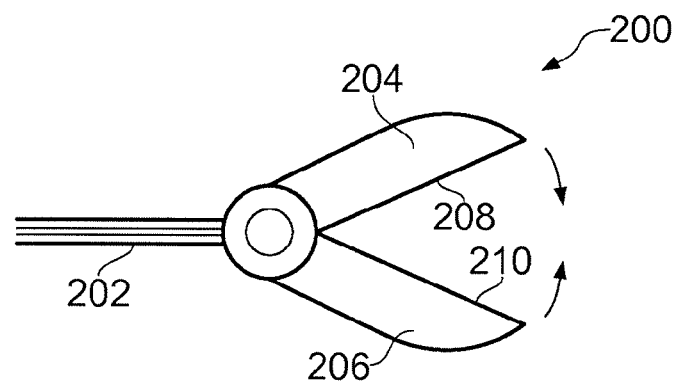
FIG. 3A is a schematic side view of vessel sealing instrument that is an embodiment of the invention.

FIG. 3A shows schematically a vessel sealing instrument 200 that is an embodiment of the invention. In this embodiment, the instrument 200 is connected to receive power through a coaxial cable 202 from an energy source (not shown) capable of generating and delivering RF EM energy and microwave EM energy separately or simultaneously. The instrument 200 has a pincer-like configuration comprising two arms 204, 206 that are hinged together to pivot between an open position and a closed position. The open position is illustrated in FIG. 3A.

In this example, tissue to be treated may be positioned and compressed or clamped between the arms 204, 206 of this instrument before the microwave and/or RF energy is supplied. The distal end of the instrument in this embodiment thus comprises opposing inner edges 208, 210 of the arms 204, 206. Each inner edge has an exposed radiating element (i.e. the bipolar radiating structure) on it, which may take one of a number of forms, as discussed below. According to the invention, each inner edge 208, 210 comprises its own antenna structure, i.e. each of the radiating inner edges 208, 210 contain radiators with a local return path so that they radiate microwave and/or RF energy into tissue in a manner that does not rely on the position of the other edge.

In one embodiment, the radiating inner edges may each comprise a travelling wave antenna structure, in which a plurality of radiating apertures (or radiating slots) increase in width as their distance from the energy source (i.e. the feed point or the distal end of the coaxial cable 202) increases. The direction of the slots may be along the direction of the arms 204, 206 or perpendicular to the direction of the arms. With this configuration, microwave energy may be radiated from the slots in a uniform manner. This arrangement is disclosed in more detail below with reference to FIGS. 10A to 10C.

In another embodiment, parallel plate transmission line structures may be fabricated onto each of the arms 204, 206, wherein the radiating edge(s) of the parallel plate transmission line structures are either arranged or positioned to radiate along the direction of the arms or perpendicular to the direction of the arms. Each radiating edge may be arranged to radiate both microwave and RF energy into the tissue or the vessel, i.e. the return path for the RF and microwave currents is local to the blade or parallel plate transmission line, thus the operation or effectiveness of the instrument is independent of the distance the jaws are from one another, therefore it is possible to use the instrument to cut and coagulate (i.e. seal) a vessel of any diameter. The device may apply a mechanical force to the vessel to assist with the overall sealing process.

The vessel sealing instrument may be used as part of an open or key-hole surgical resection or dissection device. The energy source may include a 100 W solid state power source operating at 5.8 GHz. This type of microwave EM energy may produce a depth of penetration by radiation that enables the instrument to coagulate to a depth of 4 cm along a length of 10 cm of tissue in 2 minutes (assuming that the density of whole blood is 1060 kgm$^{-3}$ and the specific heat capacity for blood is 3840 J/kgK. Following coagulation, RF EM energy can be applied to cut through the tissue. The instrument may achieve haemostasis on a bleeding liver bed or spleen by applying the radiating section of the structure over the bleeding surface to denature the ends of the bleeding vessels, constricting them to make or produce a natural ligature, which would further be plugged with coagulation. The microwave and RF EM energy may be applied simultaneously to enhance the tissue effects caused by the microwave or RF energy applied independently. The ability to deliver RF and microwave EM energy along one single channel (cable assembly) into one instrument structure makes it possible to safely arrange for the tissue to be cut using RF EM energy after it has already been coagulated using microwave EM energy.

Figure 3B:
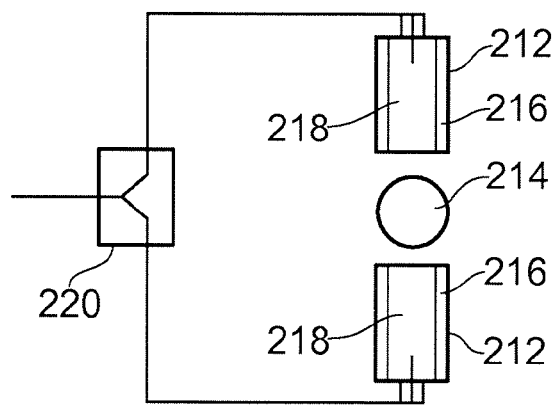
FIG. 3B is a schematic side view of an arrangement of two radiating blades that are suitable for use in an embodiment of the invention.
Figure 3C:
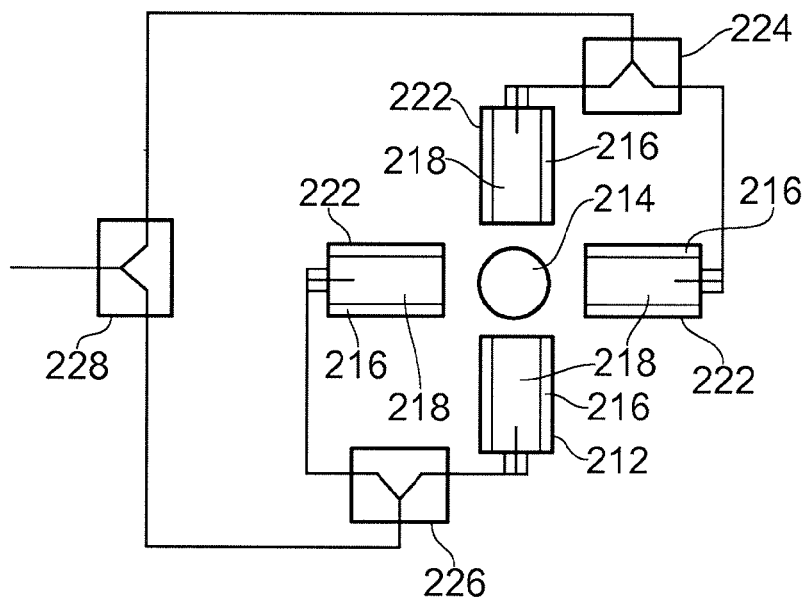
FIG. 3C is a schematic side view of an arrangement of four radiating blades that are suitable for use in an embodiment of the invention.

FIGS. 3B and 3C show two arrangements for the vessel sealing instrument, where a plurality of radiating structures (corresponding to the arms shown in FIG. 3A) deliver both RF and microwave EM energy into a vessel 214. The arms are arranged around the vessel 214 to deliver EM energy into it.

FIG. 3B shows two radiating blades 212 positioned on opposite sides of the vessel 214. Each blade 212 comprises a planar body of dielectric material 216 having a conductive material 218 (e.g. a metallised layer) formed on opposite plane surfaces thereof, e.g. in a manner similar to the bipolar antenna structure discussed above with reference to FIGS. 1 and 2. The radiating blade emits from its distal end (nearest the vessel in FIG. 3B) an EM field corresponding to the received RF and/or microwave signal. The conductive layers on a first surface of the planar body is electrically connected to the inner conductor of the coaxial cable, while the conductive layer on the second (opposite) surface is electrically connected to the outer conductor of the coaxial cable. The planar body provides a local return path for both RF and microwave currents that pass through the blade 212. In this embodiment, an equal amount of power is applied to each blade 212 by using a 3 dB power splitter 220, which may be a Wilkinson power divider, a stripline backward wave coupler or the like. The blades may be arranged so that the signal introduced into each blade has the same power and phase, but the invention is not limited to this being the case, i.e. a phase lag of 90° or 180° may be introduced to one of the blades. The phase and amplitude difference between the two blades may also be adjusted electronically by introducing power attenuators and/or variable delay lines in one or both paths between the output ports of power splitter 220 and the input port of a respective radiating blade 212. This adjustment may enable the electromagnetic radiation to be further focussed into the vessel to promote more rapid and efficient vessel sealing.

FIG. 3C shows a similar configuration to FIG. 3B, but uses four radiating blades 222 arranged around vessel 214 to deliver microwave and RF energy into vessel 214 to coagulate and cut the vessel. The blades are arranged in two opposing pairs, which close together in directions that are orthogonal in order to contact the vessel from four sides. As with FIG. 3B, each radiating blade comprises a planar body of dielectric material 216 having a conductive material 218 (e.g. a metallised layer) formed on opposite plane surfaces thereof in a way that causes the radiating blade to emit from its distal end an EM field corresponding to the received RF and/or microwave signal or through user control of the power level and duty cycle (or on/off times) of the RF and microwave energy delivered into tissue. This configuration uses three in phase 3 dB power dividers 224, 226, 228 to deliver power of equal magnitude and phase into the four radiating blades 222. If coupler losses are assumed to be negligible, then the level of power delivered into vessel 214 from each blade 222 will be a quarter of the power delivered into the input port of first power divider 228. In the arrangement shown in FIG. 3C, first power divider 228 splits the power available from the distal end of transmission line (not shown) into two equal parts and at the same phase. The power at the two outputs of first power divider 228 is then fed into the input ports of two further in phase power dividers 224, 226, which produce power with equal magnitude and same phase at their output ports to feed the input ports of four radiating blades 222 equally spaced (in terms of angle) around the vessel with their radiating edges in contact or in close proximity to the vessel when the microwave and/or RF energy sources are activated. A force may be applied to the vessel prior to activation of the microwave and/or RF energy source.

All edges of the blades 222 may be rounded so that they do not contain any sharp edges that could cut into the vessel and cause cutting by use of mechanical force rather than electrical energy. This feature prevents the vessel being ruptured when the RF and microwave energy sources are inactivated and the instrument is being positioned in the vicinity of the vessel. If the vessel is ruptured by mechanical means then blood loss may occur unnecessarily.

FIGS. 4A and 4B show a vessel sealing instrument 230 that is another embodiment of the invention. In the process of cutting through a vessel, it is necessary to ensure that a 'bung' or 'plug' of coagulated material with a large enough depth, i.e. 2 mm to 5 mm, is present at the separated ends of the vessel following the cutting procedure to prevent unwanted fluid (e.g. blood) leakage. For this reason it is important that the cut takes place within (preferably at the centre of) a coagulated region, e.g. 2 mm along a 4 mm coagulated length or 5 mm along a 10 mm coagulated length. The present invention facilitates this process because the coagulation or collagen denaturisation and cutting are performed with the tool in the same position, which is automatically centrally located in a region of coagulation or collagen denaturisation. The use of microwave energy at a frequency of 5.8 GHz helps promote collagen denaturisation to produce a useful plug at the ends of the divided vessel. The 5.8 GHz focussed source promotes the development of a plug that can be used to promote collagenesis since the depth of penetration of the electric is field, which is transferred into heat to form the plug, reduces to 37% of its maximum value over a depth of between 6 mm and 7 mm in the tissue types encountered by the instrument, i.e. blood vessels, blood, liver and spleen.

FIG. 4A shows that the vessel sealing instrument 230 has a set of jaws at its distal end, the jaws comprising a pair of movable arms 232, 234. In FIG. 4A the jaws are in a closed position with vessel 236 clamped in between. RF and microwave EM energy can be fed into the instrument 230 using an RF/microwave connector 238 that is connectable to a flexible coaxial cable (not shown) which conveys the RF and microwave energy from a suitable generator (not shown). The RF and microwave EM energy received at the connector 236 may be transported into a handheld body 240 of the instrument 230 using a transmission line or microwave/RF cable assembly 242. The handheld body 240 may be designed to enable the user to hold and operate the instrument in a controllable and comfortable manner. A handgrip 244 and trigger 246 may fit in a user's hand to enable easy operation. A shaft 248 connects the handheld body 240 to the set of jaws. The transmission line or microwave/RF cable assembly 242 continues through the handheld body 240 and travels within the shaft 248 to the set of jaws. At the distal end of the shaft 248, the transmission line or microwave/RF cable assembly 242 connects to power splitting circuitry (not shown here, but similar to that discussed above with reference to FIG. 3B), which splits the RF and/or microwave EM energy into two parts. Each part is connected to a respective antenna structure, the antenna structure being formed on opposing inner surfaces of the arms 232, 234. As above, the circuit may split the input signal into parts having equal magnitude and phase.

The antenna structure on each arm 232, 234 of the set of jaws may be a radiating blade as discussed above with reference to FIGS. 1 and 2. Alternatively it may have any of the antenna structure discussed below.

FIG. 4B shows the vessel sealing instrument 230 with the set of jaws in an open position and illustrates a possible arrangement for radiating blades 250, 252 on the arms 232, 234. Radiating blades 250, 252 may be arranged such that their radiating edges extend in the same direction as their respective arm 232, 234. This arrangement may be preferred because jaws are suitably orientated for clamping the vessel without twisting it. Thus, the instrument may be positioned for operation with minimal damage to the vessel.

Figure 5A:
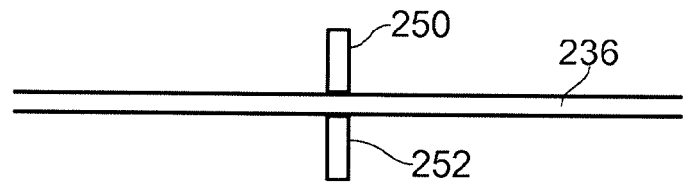
FIGS. 5A to 5C show the steps in a vessel sealing and cutting process using a vessel sealing instrument that is an embodiment of the invention.
Figure 5B:
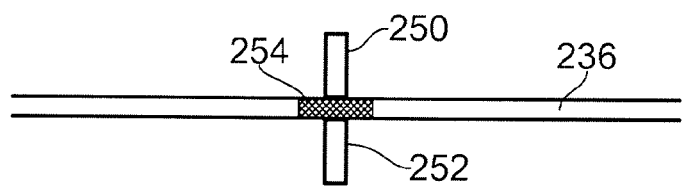
Figure 5C:
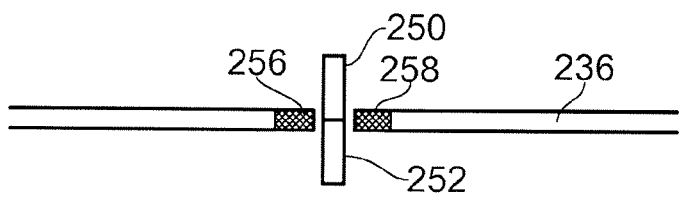

FIGS. 5A, 5B and 5C illustrate schematically the vessel sealing and cutting process. FIG. 5A shows two radiating blades 250, 252 positioned (before the energy source is activated) in contact with vessel 236 on opposite sides thereof, i.e. the radiating blades face each other across the vessel. It may also be necessary to apply a mechanical force at this stage of the vessel sealing process. For example, mechanical pressure from the forceps or jaws maybe applied to press the walls of the vessel together to push the intra luminal contents out sideways and leave the inner and outer vessel walls intact and in contact with one another. A first phase involving the application of microwave energy to the outer wall may then commence to initiate the collagen denaturisation process, which mobilises the strands. This may be followed by a second phase that involves the application of a second dosage of microwave energy (this may be delivered using a different power/time waveform) to fix the collagen together. This may then be followed by a relaxation phase to allow the tissue to cool, followed by a final phase that involves the application of RF energy to the blades to transect or cut the vessel into two. FIG. 5B illustrates the situation where the microwave and RF energy is applied to the vessel 236 through the radiating blades 250, 252. Two regions of coagulation are formed, one extending away from each radiating blade 250, 252 until they meet to form a plug 254 of coagulant. While the regions of coagulation grow away from their respective radiating blade 250, 252, a flow channel still exists in the vessel 236 to allow blood flow to take place, albeit in a restricted manner. Because each radiating blade 250, 252 operates independently (i.e. has its own local return path for the RF signal), the formation of each region of coagulation is also independent. This may ensure a more uniform plug 254 is produced, i.e. may avoid regions of weak binding to the vessel wall which may rupture when the vessel is severed. In particular, this configuration may facilitate the formation of a symmetrical (e.g. relative to a notional axis through the centre of the vessel) plug of coagulant 254 that allows new collagen to invade the old collagen matrix to allow the vessel to 'grow' in the closed position.

In the invention, RF EM energy and microwave EM energy may be emitted simultaneously to perform the sealing (coagulating) and cutting action. The delivery profile of each type of energy may be configured to correspond to the action it is to perform. Thus, the microwave EM energy may be arranged to seal the vessel by causing coagulation. The delivery profile for the microwave EM energy may be selected to coagulate to a distance of x mm. The RF EM energy, on the other hand, may be arranged to cut the vessel. The delivery profile for the RF EM energy may therefore be selected to cut to a distance of $$\frac{x}{2}$$

mm. The RF cutting action therefore extends only a limited distance into the region affected by the microwave sealing action. This may ensure that the vessel is not cut before it is sealed. In addition, the activation of the RF EM energy may occur a predetermined amount of time after the microwave EM energy has been applied, to permit the region of coagulation to form. In practice, the process may comprise repeatedly applying pulses (e.g. offset pulses) of microwave EM energy and RF EM energy.

FIG. 5C illustrates the situation where original vessel 236 has been sealed and parted. Two separate vessels are formed and the plug 254 of coagulant is separated into two terminal blocking regions 256, 258 which prevent blood leaking from the ends of the separated vessel. The two radiating blades 250, 252 may contact each another at the end of the vessel sealing process. It may be desirable to arrange the radiating blades in such a manner that enables two or more seals to be made to the vessel at the end that is closest to the heart, i.e. the instrument may contain a plurality of radiating blades. It may be desirable not to totally constrict the vessel when making the first seal, but totally constrict it when making the second seal.

Figures 6A, 6B:
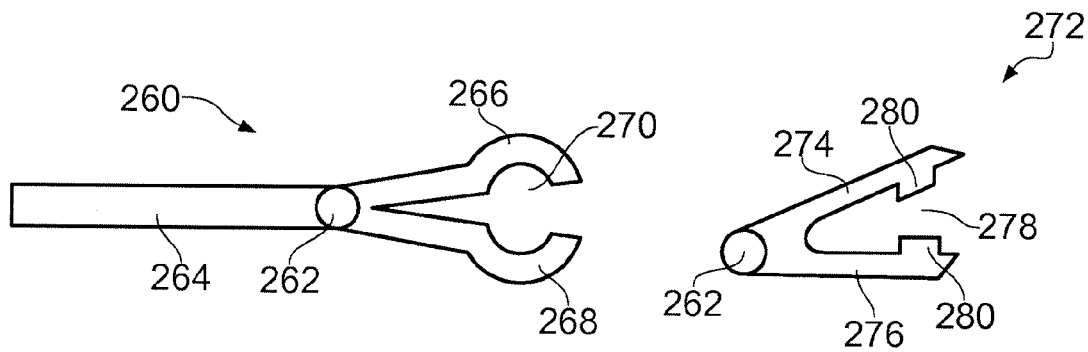
FIG. 6A is a side view of a vessel sealing instrument that is another embodiment of the invention.
FIG. 6B is a side view of a vessel sealing instrument that is yet another embodiment of the invention.

FIGS. 6A and 6B illustrate further embodiments of the invention. FIG. 6A shows the distal end 260 of a vessel sealing instrument similar to that discussed above with reference to FIGS. 4A and 4B. In this embodiment, a sleeve 264 housing the coaxial feed cable terminates at a hinge 262, about which two opposing arms 266, 268 pivot to open and close a clamping region 270 therebetween. The open/close action may be user-controllable, e.g. using guide wires (not shown) which travel through the sleeve 264. In use, a vessel to be sealed and/or cut is positioned in the clamping region, where it may be physically held between the opposing arms 266, 268 to apply a force to partially close the vessel, while RF and/or microwave EM energy is applied. In this embodiment, the inner (i.e. facing) surfaces of each arm 266, 268 includes a concave recessed portion. When the arms 266, 268 are closed, the recessed portions combine to form a hole for receiving the vessel. The radiating structures of the instrument are each located within the concave recessed portion of a respective arm 266, 268.

FIG. 6B shows another distal end 272 of a vessel sealing instrument. In this example, the sleeve (not shown) also terminates at a hinge 262, about which a pair of opposing arms 274, 276 pivot to open and close a clamping region 278 therebetween. The arms 274, 276 resemble a pair of forceps, and each have on their inner (facing) surface a projection 280 which comprises the radiating structure for that arm. When the arms 274, 276 are closed, the flat outer surfaces of the opposing projections 280 meet in the clamping region 278. This embodiment therefore permits physical pressure to be applied across the vessel in addition to the RF and microwave EM energy from the radiating structures. This pressure may be required to assist in the sealing process when large vessels are involved.

FIGS. 7 to 9 show a number of further examples of how radiating blades for emitting microwave and RF EM energy into vessels can be arranged at the distal end of a vessel sealing instrument.

FIG. 7A shows an arrangement where the edges of the radiating structures 282, 284 are concave and conform to the shape of the vessel when the arms 286, 288 onto which they are formed are pivoted closed around vessel 290. The radii of the concave surfaces of radiating structures 282, 284 is set to be large enough to ensure that the vessel 290 sits within the concave surfaces during the sealing process. For example, the radii of the concave surfaces may be 5 mm and the diameter of the vessel may be 4 mm. The microwave and RF EM energy is delivered to the radiating structures 282, 284 via a microwave cable assemble contained within delivery shaft, as explained above. In this particular arrangement, it may be preferable for the radiating structures 282, 284 to protrude slightly from their respective arms 286, 288, e.g. by 0.5 mm, to allow the radiating surfaces to be in contact with the vessel throughout the coagulation-cutting process. This configuration may ensure that vessels with a smaller radii than the radii of the radiating blades can still be effectively sealed and cut. In FIG. 7A, the radiating structures 282, 284 are located in line with the arms 286, 288.

FIG. 7B shows a front view of a similar arrangement to FIG. 7A, except that the radiating structures 282, 284 are perpendicular to the length of the arms 286, 288.

FIG. 8A shows an arrangement where the edges of the radiating structures 282, 284 that deliver microwave and RF EM energy into vessel 290 are convex. The radii of the convex surfaces of radiating structures 282, 284 should be large enough to ensure that the vessel 290 being sealed is exposed to the microwave and RF EM energy, i.e. the radii of the convex surfaces may be 5 mm and the diameter of the vessel may be 4 mm. In FIG. 8A, the radiating structures 282, 284 are located in line with the arms 286, 288.

FIG. 8B shows a front view of a similar arrangement to FIG. 8A, except that the radiating structures 282, 284 are perpendicular to the length of the arms 286, 288.

FIG. 9A shows an arrangement where the edges of the radiating structures 282, 284 that deliver microwave and RF EM energy into vessel 290 are flat (it may be preferable for the edges to be slightly rounded off at the corners to remove any possibility of vessel damage due to sharp edges). In FIG. 9A, the radiating structures 282, 284 are located in line with the arms 286, 288.

FIG. 8B shows a front view of a similar arrangement to FIG. 8A, except that the radiating structures 282, 284 are perpendicular to the length of the arms 286, 288.

FIGS. 10A, 10B and 10C illustrate a further embodiment of the invention. In this embodiment, the vessel sealing instrument 300 uses a travelling wave antenna structure to deliver the microwave and RF EM energy into the biological tissue.

FIG. 10A shows the whole instrument 300. This embodiment comprises a pair of forceps 302, 304 at the distal end of a shaft 306. The shaft 306 is connected to a handheld unit 308, which includes a finger grip 310 (for opening and shutting the forceps 302, 304) and trigger 312. It may be preferable for this structure to apply RF energy between the two blades, i.e. use one blade or arm as the active and the second blade or arm as the return. The trigger 312 is used to activate delivery of microwave and/or RF EM energy from antenna structures formed on the inner surfaces of the forceps 302, 304. The handheld unit 308 is connected to a energy source (not shown) via a flexible coaxial cable 314. Pressing the trigger may cause control electronics within handheld unit to issue an activation instruction to control electronics in the energy source. Communications between the handheld unit and the energy source may be carried by suitable wiring in the flexible coaxial cable 314 or may be done wirelessly. The flexible coaxial cable 314 may extend inside the handheld unit all the way to the distal end of the shaft 306. The power available at this point is split into two equal parts using appropriate microwave/RF power dividers (discussed above) contained within the shaft 306. It may be preferable for in-phase power dividers to be used in order to ensure that the EM radiation delivered independently from the antenna structures is in phase to achieve the desired tissue effect.

FIG. 10B shows a close up view of the forceps 302, 304. The inner surface of each finger of the forceps 302, 304 has a travelling wave antenna structure 316 formed thereon. As shown in FIG. 10C, each travelling wave antenna structure 316 comprises a slotted layer of metallization 320 formed on an outward facing (i.e. front) surface of a piece of dielectric material 318. A conductive feed line 322 is formed on the inward facing (i.e. back) surface of the dielectric material 318, and is connected to receive the microwave and/or RF EM energy from the microwave/RF power divider mentioned above.

The slotted layer of metallization 320 is configured such that the microwave and/or RF EM energy used to coagulate or denature collagen within the vessel is radiated through the dielectric material exposed at the slots 324. The regions of metallization located adjacent to slots 324 provide the ground plane or preferred path for the return currents (microwave and RF) to flow. The RF field will be between the active and return edges of the travelling wave structures and the metallization may be cut back along the edges where the cutting action is not required. The RF EM energy will not radiate from the slots since the aperture sizes will be such that the wave at RF frequencies will be cut-off.

As shown in FIG. 10B, the length of the travelling wave antenna structure 316 is along (parallel to) the length of its respective finger 304, but it may be preferable for the structure to be angled (e.g. at 90°) to the finger.

As shown in FIG. 10C, the length of slots 324 may increase with increasing distance away from the microwave generator. The spacing between radiating slots, the width of the slots and the length of the slots can be optimised to radiate uniform microwave energy into representative biological tissue at the microwave frequency of interest using electromagnetic field modelling tools such as Ansoft HFSS or CST Microwave Studio. The advantage of such travelling wave antenna structures is that the microwave radiation is uniform along the entire length of the structure, which ensures a uniform region of tissue coagulation is achieved. This particular arrangement of the instrument may achieve the desired tissue effects without the use of RF energy.

Figure 11A:
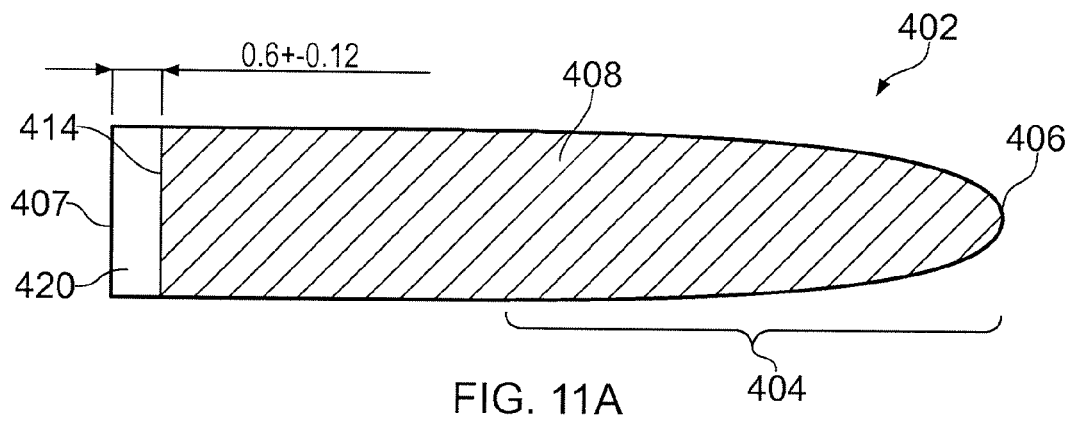
FIGS. 11A, 11B and 11C are a top view, side view and bottom view respectively of energy delivery structure suitable for use in a vessel sealing instrument that is another embodiment of the invention.
Figure 11B:
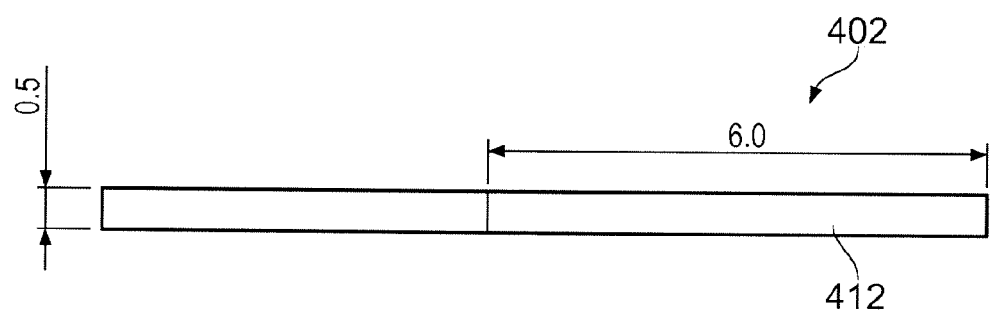
Figure 11C:
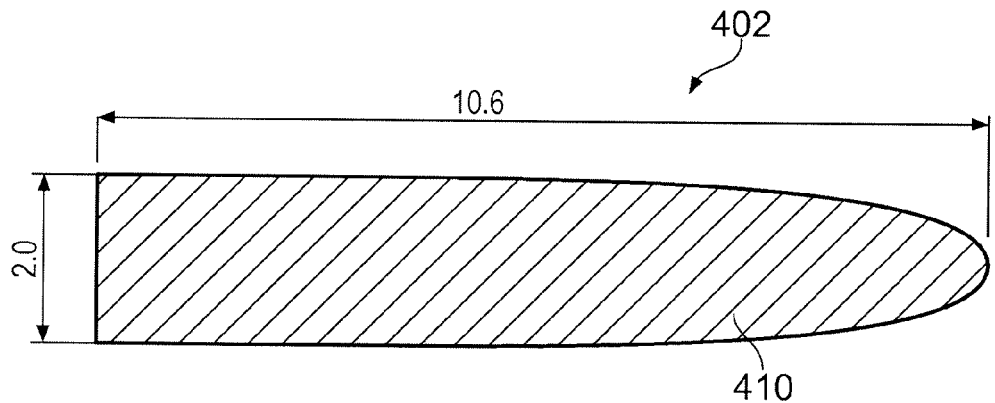

In the instruments discussed above with reference to FIGS. 1 and 2, the energy delivery structure (i.e. radiating "blade") was a rectangular transmission line structure. FIGS. 11A, 11B and 11C depict various views of a transmission line-type blade 402 that is a development of the known rectangular transmission line. In this example, the distal end 404 of the blade tapers towards a curved tip 406. The overall length of the blade from proximal end 407 to distal tip 406 is 10.6 mm in this embodiment. The blade has a portion of constant width (or 2.0 mm) at the proximal end 407, before the tapering takes place over the final 6.0 mm of the blade's length. Different curvatures can be chosen, depending on the desired radiation pattern.

Similarly to the blade discussed in FIGS. 1 and 2, the blade 402 in this example comprises a body of dielectric material (having a thickness of 0.5 mm) having conductive layers formed on its major (i.e. top and bottom) surfaces 408, 410. The conductive layers are preferably metallisation layer e.g. of PtAg. The side edges 412 are exposed dielectric (i.e. are without metallisation). Different thicknesses of dielectric material can be chosen.

Similarly to the blade discussed in FIGS. 1 and 2, a gap 420 is provided between the proximal edge 414 of the upper conductive layer 408 and the proximal end 407 of the blade (which corresponds to the distal end of the coaxial cable in use). This gap assists with the impedance match between the energy delivery structure (that forms a part of the source) and the load impedance presented to that structure by the biological load.

The shape of blade discussed with reference to FIGS. 11A, 11B and 11C is capable of radiating from its side edges as well as its distal end. Accordingly, in an unillustrated embodiment of the invention, a vessel sealing instrument may be provided that uses a pair of the radiating blades shown in FIGS. 11A, 11B and 11C arranged side-by-side whereby a vessel can be located between the side edges of the blades to be sealed. One or both blade may be pivotally mounted on an instrument shaft to allow the pair of blades to be open and shut. This arrangement can enable the instrument also to be used to apply a clamping pressure to the vessel being sealed.

The instrument described above may be used in laparoscopic or open surgery to carry out resection of vascular organs contained within the animal and human body. Alternatively or additionally, the instrument may be suitable for use as a thermal ligature device.

The invention claimed is:

1. An electrosurgical instrument for performing resection or dissection by applying to a biological tissue radiofrequency electromagnetic RF EM energy having a first frequency and microwave EM energy having a second frequency higher than the first frequency, the instrument comprising:
a handheld body having an elongate probe member extending therefrom, the elongate probe member having at its distal end an instrument tip comprising a clamping mechanism having a first clamping member and a second clamping member that are movable relative to each other between an open configuration for receiving a biological vessel between a first surface on the first clamping member and a second surface on the second clamping member, the first surface and the second surface being opposite to one another in the instrument tip, and a closed configuration for contacting opposite sides of the received biological vessel, wherein the first clamping member includes a first energy delivery structure comprising a body made of a first dielectric material, and a first conductive element and a second conductive element which are separated by the first dielectric material; and a coaxial feed cable connected to the handheld body, the coaxial feed cable comprising an inner conductor, an outer conductor coaxial with the inner conductor, and a second dielectric material separating the outer conductor and the inner conductors, the coaxial feed cable being for conveying to the handheld body, simultaneously or separately, an RF signal having the first frequency and a microwave signal having the second frequency;

wherein the inner conductor is electrically connected to the first conductive element of the first energy delivery structure and the outer conductor is electrically connected to the second conductive element of the first energy delivery structure to enable the first surface to emit independently the RF signal and the microwave signal, and wherein the first conductive element of the first energy delivery structure and the second conductive element of the first energy delivery structure are arranged at the first surface to act:

as an active electrode and a return electrode to transfer RF EM energy into the biological tissue by conduction, and as an antenna to radiate microwave EM energy into biological tissue from the first surface.

2. The instrument according to claim 1, wherein the second clamping member possesses a second energy delivery structure comprising a body made of the first dielectric material, and a first conductive element and a second conductive element which are separated by the first dielectric material, wherein the inner conductor is connected to the first conductive element of the second energy delivery structure and the outer conductor is connected to the second conductive element of the second energy delivery structure, the first conductive element of the second energy delivery structure and the second conductive element of the second energy delivery structure are arranged at the second surface to act:

as an active electrode and a return electrode to transfer RF EM energy into the biological tissue by conduction, and as an antenna to radiate microwave EM energy into biological tissue from the second surface, whereby the first surface and the second surface are independently controllable to deliver one or both of the RF EM energy and microwave EM energy into the biological tissue.

3. The instrument according to claim 2, wherein the first surface and the second surface are rounded or curved.

4. The instrument according to claim 2, wherein the shape of the first surface and the second surface is concave or convex or flat.

5. The instrument according to claim 1, wherein the first conductive element and the second conductive element and the first dielectric material on the first clamping member are configured as a bipolar emitting structure, having a local return path.

6. The instrument according to claim 5, wherein the bipolar emitting structure is a parallel plate arrangement in which the first dielectric material is a planar sheet and the first conductive element and the second conductive element are conductive layers formed on opposite sides of the planar sheet, a radiating edge of the parallel plate arrangement being exposed on the first surface, which is a vessel contact surface of the first clamping member.

7. The instrument according to claim 6, wherein the exposed radiating edge of the parallel plate arrangement is aligned with an axial length of the first clamping member.

8. The instrument according to claim 1, wherein the first clamping member and the second clamping member are arranged to apply a force to the received biological vessel when in the closed configuration.

9. The instrument according to claim 1, wherein the first clamping member and the second clamping member have a plurality of energy delivery structures arranged along their respective opposed surfaces.

10. The instrument according to claim 1, wherein the first dielectric material, the first conductive element, and the second conductive element are configured as a travelling wave antenna.

11. The instrument according to claim 10, wherein the first conductive element is a layer of metallisation covering an outward facing surface of the first dielectric material at the first surface of the first clamping member, a plurality of slots being formed in the layer of metallisation to expose the first dielectric material.

12. The instrument according to claim 1, wherein the handheld body comprises a clamp operating actuator for controlling movement of the first clamping member and the second clamping member, and an energy activation switch that is operable independently of the clamp operating actuator to activate energy delivery from the first surface.

13. The instrument according to claim 1, wherein the coaxial feed cable extends through the housing to connect to a power splitting arrangement, which is operable to split one or both of the RF EM energy and microwave EM energy conveyed by the coaxial feed cable between first conductive element and the second conductive element on the first clamping member.

14. The instrument according to claim 1, wherein the energy delivery structure is configured to create an omnidirectional microwave EM field with a depth of penetration into the vessel of between 6 mm and 7 mm.

15. The instrument according to claim 1, wherein the biological vessel is a blood vessel.

16. A surgical vessel sealing method of using an electrosurgical resection instrument that is arranged to apply to a biological tissue radiofrequency electromagnetic RF EM energy having a first frequency and microwave EM energy having a second frequency higher than the first frequency, the electrosurgical resection instrument comprising:

a handheld body having an elongate probe member extending therefrom, the elongate probe member having at its distal end an instrument tip comprising a clamping mechanism having a first clamping member and a second clamping member that are movable relative to each other between an open configuration for receiving a biological vessel between a first surface on the first clamping member and a second surface on the second clamping member, the first surface and the second surface being opposite to one another in the instrument tip, and a closed configuration for contacting opposite sides of the received biological vessel, wherein the first clamping member includes a first energy delivery structure comprising a body made of a first dielectric material, and a first conductive element and a second conductive element which are separated by the first dielectric material; and a coaxial feed cable connected to the handheld body, the coaxial feed cable comprising an inner conductor, an outer conductor coaxial with the inner conductor, and a second dielectric material separating the outer conductor and the inner conductor, the coaxial feed cable being for conveying to the handheld body, simultaneously or separately, an RF signal having the first frequency and a microwave signal having the second frequency;

wherein the inner conductor is electrically connected to the first conductive element of the first energy delivery structure and the outer conductor is electrically connected to the second conductive element of the first energy delivery structure to enable the first surface to emit independently the RF signal and the microwave signal, and wherein the first conductive element of the first energy delivery structure and the second conductive element of the first energy delivery structure are arranged at the first surface to act:

as an active electrode and a return electrode to transfer RF EM energy into the biological tissue by conduction, and as an antenna to radiate microwave EM energy into biological tissue from the first surface, wherein the surgical vessel sealing method comprises:

(i) a mechanical step of applying pressure from the clamping mechanism to press the walls of the biological vessel together so that intra-luminal contents are pushed out sideways leaving an inner wall and an outer wall of the biological vessel intact and in contact with one another;

(ii) a first electrical heating step of applying one or both of the microwave EM energy or RF EM energy having a first waveform for initiating collagen denaturisation and mobilisation of denatured collagen strands; and (iii) a second electrical heating step of applying one or both of the microwave EM energy or RF EM energy having a second waveform for fixing or fusing the collagen together.

17. The method of claim 16 including, after the second electrical heating step, a cutting step of applying RF EM energy to the vessel from a radiating edge of the instrument.

* * * * *